United States Patent
Albert et al.

(10) Patent No.: US 7,326,801 B2
(45) Date of Patent: Feb. 5, 2008

(54) 2-AMINO-PROPANOL DERIVATIVES

(75) Inventors: Rainer Albert, Basel (CH); Thomas Baumruker, Moedling (AT); Volker Brinkmann, Freiburg (DE); Sylvain Cottens, Witterswil (CH); Klaus Hinterding, Rümmingen (DE); Christos Papageorgiou, Riedisheim (FR); Eva Erika Prieschl-Strassmayr, Vienna (AT)

(73) Assignee: Novartis AG, Basel (CH)

( * ) Notice: Subject to any disclaimer, the term of this patent is extended or adjusted under 35 U.S.C. 154(b) by 413 days.

(21) Appl. No.: 10/472,127

(22) PCT Filed: Mar. 26, 2002

(86) PCT No.: PCT/EP02/03389

§ 371 (c)(1),
(2), (4) Date: Mar. 18, 2004

(87) PCT Pub. No.: WO02/076995

PCT Pub. Date: Oct. 3, 2002

(65) Prior Publication Data

US 2004/0147490 A1    Jul. 29, 2004

(30) Foreign Application Priority Data

Mar. 26, 2001 (GB) ................... 0107506.8
Mar. 26, 2001 (GB) ................... 0107507.6
Apr. 3, 2001 (GB) ................... 0108346.8

(51) Int. Cl.
*A61K 31/662* (2006.01)
*C07F 9/09* (2006.01)

(52) U.S. Cl. ............... 558/172; 558/169; 558/166

(58) Field of Classification Search ................ 558/172, 558/169, 166
See application file for complete search history.

(56) References Cited

U.S. PATENT DOCUMENTS 6,437,165 B1 * 8/2002 Mandala et al. ............ 558/169
2003/0236297 A1 12/2003 Nishi et al. .................. 514/438

FOREIGN PATENT DOCUMENTS

| EP | 0 627 406 | 12/1994 |
| EP | 0 778 263 | 6/1997 |
| EP | 1 002 792 | 5/2000 |
| WO | 94/28004 | 12/1994 |
| WO | 02/18395 | 3/2002 |

OTHER PUBLICATIONS

Adachi et al., "Design, Synthesis, and Structure-Activity Relationships of 2-Substituted-2-Amino-1,3-Propanediols: Discovery of a Novel Immunosuppressant, FTY720", Bioorganic & Medicinal Chemistry Letters, vol. 5, No. 8, pp. 853-856 (1995).

Kley et al., "Synthesis and PLA2-Inhibitory Properties of 2(R)-Acetamino-Alkylphosp Homethanols with a Variable Aggregate Anchor", Bioorganic & Medicinal Chemistry Letters, vol. 9, No. 2, pp. 261-264 (1999).

* cited by examiner

Primary Examiner—Laura L. Stockton

(57) ABSTRACT

Compounds of formula I

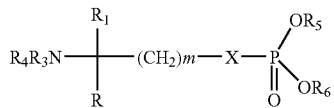

wherein m, R, $R_1$ and $R_3$ to $R_6$ are as defined in the specification, m, is 1, 2 or 3 and X is O or a direct bond, and the corresponding unphosporylated compounds have interesting properties, e.g. immunosuppressive properties.

4 Claims, No Drawings

2-AMINO-PROPANOL DERIVATIVES

The present invention relates to 2-amino-propanol derivatives, process for their production and pharmaceutical compositions containing them.

More particularly the present invention provides a compound of formula I

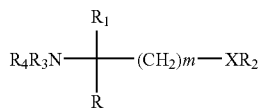

wherein
m is 1, 2 or 3;
X is O or a direct bond;
$R_1$ is H; $C_{1-6}$ alkyl optionally substituted by OH, acyl, halogen, cycloalkyl, phenyl or hydroxy-phenylene; $C_{2-6}$alkenyl; $C_{2-6}$alkynyl; or phenyl optionally substituted by OH;
$R_2$ is

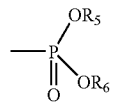

wherein $R_5$ is H or $C_{1-4}$alkyl optionally substituted by 1, 2 or 3 halogen atoms, and $R_6$ is H or $C_{1-4}$alkyl optionally substituted by halogen;
each of $R_3$ and R4, independently, is H, $C_{1-4}$alkyl optionally substituted by halogen, or acyl, and
R is $C_{13-20}$alkyl which may optionally have in the chain an oxygen atom and which may optionally be substituted by nitro, halogen, amino, hydroxy or carboxy; or a residue of formula (a)

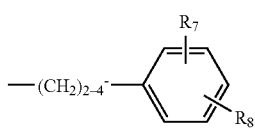

wherein $R_7$ is H, $C_{1-4}$alkyl or $C_{1-4}$alkoxy, and $R_8$ is substituted $C_{1-20}$alkanoyl, phenyl$C_{1-14}$alkyl wherein the $C_{1-14}$alkyl is optionally substituted by halogen or OH, cycloalkyl$C_{1-14}$alkoxy or phenyl$C_{1-14}$alkoxy wherein the cycloalkyl or phenyl ring is optionally substituted by halogen, $C_{1-14}$alkyl and/or $C_{1-4}$alkoxy, phenyl$C_{1-4}$alkoxy$C_{1-14}$alkyl, phenoxy$C_{1-14}$alkoxy or phenoxy$C_{1-4}$alkyl, R being also a residue of formula (a) wherein $R_8$ is $C_{1-14}$alkoxy when $R_1$ is $C_{1-4}$alkyl, $C_{2-6}$alkenyl or $C_{2-6}$alkynyl, in free form or in salt form.

Halogen is F, Cl, Br or I. Alkyl or alkoxy may be straight or branched chain.

Cycloalkyl is preferably $C_{3-10}$cycloalkyl, more preferably $C_{3-8}$cycloalkyl and includes, for example, cyclopropyl, cyclobutyl, cyclopentyl, cyclohexyl or cycloheptyl.

Acyl is optionally substituted alkanoyl or aroyl, in which alkanoyl is a straight- or branched chain alkanoyl having 1 to 20 carbon atoms, and is e.g. formyl, acetyl, propionyl, butanoyl isobutyryl, pentanoyl or hexanoyl. Examples of aroyl include e.g. benzoyl. $C_{1-20}$alkanoyl is preferably $C_{2-14}$alkanoyl and may optionally be substituted, e.g. by phenyl or cycloalkyl, e.g. cyclohexyl, preferably at the terminal position. Examples of substituted alkanoyl include e.g. benzoyl, phenylacetyl, phenylpropionyl, phenylbutanoyl, cyclohexylacetyl, cyclohexylproplonyl, cyclohexylbutanoyl or cyclohexylbutanoyl.

In phenyl$C_{1-14}$alkyl or phenyl$C_{1-14}$alkoxy the $C_{1-14}$alkyl or $C_{1-14}$alkoxy moiety preferably contains 1 to 10 carbon atoms.

When $R_1$ is substituted $C_{1-6}$alkyl, it may be $C_{1-6}$alkyl substituted by OH, preferably at the terminal position, or $C_{1-6}$alkyl substituted by 1, 2 or 3 substituents selected from acyl, halogen, cycloalkyl, phenyl and hydroxy-phenylene.

In the compounds of the invention, the following significances are preferred individually or in any sub-combination:
1. m is 1 or 2, preferably 1.
2. X is O.
3. $R_1$ is $C_{1-6}$alkyl optionally substituted by OH; $C_{2-6}$alkenyl; or $C_{2-6}$alkynyl.
4. Each of $R_3$ and $R_4$ is H.
5. Each of $R_5$ and $R_6$ is H.
6. R is a residue of formula (a).
7. $R_7$ is H.
8. $R_7$ is $C_{1-4}$alkoxy, e.g. methoxy.
9. $R_8$ is substituted $C_{1-20}$alkanoyl, phenyl$C_{1-4}$alkyl wherein the $C_{1-14}$alkyl is substituted by halogen or OH, cycloalkyl$C_{1-14}$alkoxy, or phenyl$C_{1-14}$alkoxy wherein the phenyl ring is optionally substituted by halogen, $C_{1-4}$alkyl and/or $C_{1-4}$alkoxy.
10. $R_1$ is $C_{2-6}$alkenyl or $C_{2-6}$alkynyl and R is a residue of formula (a) wherein $R_8$ is $C_{1-14}$alkoxy.
11. R is a residue of formula (a) wherein $R_8$ is $C_{4-8}$alkoxy.
12. In the residue of formula (a) —$CH_2)_{2-4}$— is —$CH_2$—$CH_2$—.
13. $R_8$ is in meta or para position to —$(CH_2)_{2-4}$—, preferably in para.
14. $R_7$ is in ortho to $R_8$.

Compounds of formula I may exist in free form or in salt form, e.g. addition salts with e.g. inorganic acids, such as hydrochloride, hydrobromide or sulfate, salts with organic acids, such as acetate, fumarate, maleate, benzoate, citrate, malate, methanesulfonate or benzenesulfonate salts; when $R_5$ or $R_6$ is H, $R_2$ may also be present in salt form, e.g. an ammonium salt or salts with metals such as sodium, potassium, calcium, zinc or magnesium, or a mixture thereof. Compounds of formula I and their salts in hydrate or solvate forms are also part of the invention.

When the compounds of formula I have one or more asymmetric centers in the molecule, various optical isomers are obtained. The present invention also encompasses enantiomers, Tacemates, diastereoisomers and mixtures thereof. For example, the central carbon atom bearing R and $R_1$ may have the R or S configuration. Moreover, when the compounds of formula I include geometric isomers, the present invention embraces cis-compounds, transcompounds and mixtures thereof. Similar considerations apply in relation to starting materials exhibiting asymmetric carbon atoms or unsaturated bonds as mentioned above.

Preferred compounds of formula I are e.g. the monophosphate of 2-amino-2-tetradecyl-1,3-propanediol, phosphoric acid mono-{2-amino-2-hydroxymethyl-4-[4-(5-phenyl-pentanoyl)-phenyl]-butyl}ester and phosphoric acid mono-{2-amino-2-hydroxymethyl-4-[4-(7-phenyl-heptanoyl)-phenyl]-butyl}ester.

The present invention also includes a process for the preparation of a compound of formula I which process comprises removing the hydrolysable groups present in $R'_2$ and the amino protecting group $R'_4$ in a compound of formula II

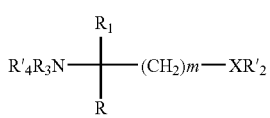

wherein m, X, $R_1$ and $R_3$ are as defined above, and $R'_2$ is

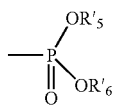

each of $R'_5$ and $R'_6$, independently, is a hydrolysable group, and $R'_4$ is an amino protecting group, and, where required, converting the compounds of formula I obtained in free form into the desired salt form, or vice versa.

Preferably $R'_5$ and $R'_6$ are identical and have the significance of e.g. phenyl or benzyl or form together a cyclic system such as in 1,5-dihydro-2,4,3-benzodioxaphosphepin. Examples of suitable amino protecting groups as $R'_4$ are e.g. as disclosed in "Protective Groups in Organic Synthesis" T. W. Greene, J. Wiley & Sons NY, $2^{nd}$ ed., chapter 7, 1991, and references therein, e.g. acyl, e.g. tert.-butoxy-carbonyl, benzyloxycarbonyl, 9-fluorenyl methoxy carbonyl, trifluoroacetyl, trimethylsilylethanesulfonyl and the like.

The removal of the amino protecting group and/or of $R'_5$ or $R'_6$ groups in the compounds wherein X is O may conveniently be performed according to methods known in the art, e.g. by hydrolysis, e.g. in a basic medium, for example using a hydroxide such as barium hydroxide. It may also be performed by hydrogenolysis, e.g. in the presence of Pearlman's catalyst, e.g. as disclosed in J. Org. Chem., 1998, 63, 2375-2377. The removal of the amino protecting group and/or of $R'_5$ or $R'_6$ groups in the compounds wherein X is a direct bond may be conveniently performed according to methods known in the art, e.g. by hydrolysis, e.g. in an acidic medium, by hydrogenolysis or e.g. as disclosed by G. Ösapay et al. Tetrahedron 43 (13), 2977-2983.

The compounds of formula II, used as starting materials, and salts thereof are also novel and form part of the present invention.

Compounds of formula II wherein X is O may be prepared by reacting a compound of formula IIIa

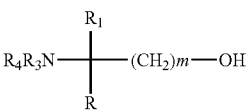

wherein m, R, $R_1$, $R_3$ and $R_4$ are as defined above, with a phosphorylating agent, e.g. a phosphorochloridate, e.g. diphenylchlorophosphate or dibenzylchlorophosphate, cyanoethylphosphate, a phosphoramidate such as N-phenyl phosphoramidate, 3-(diethylamino)-1,5-dihydro-2,4,3-benzodioxaphosphepin and the like. The reaction may be carried out according to methods known in the art, e.g. as disclosed in J. Org. Chem. supra. In the compounds of formula IIIa the amino group is preferably in protected form, as $R'_4$ when $R_4$ is other than acyl.

Compounds of formula II wherein X is a direct bond may be prepared by reacting a compound of formula IIIb

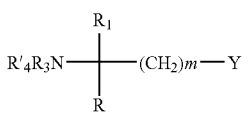

wherein $R_1$, $R_3$, $R'_4$ and m are as defined above, and

Y is a leaving group, e.g. Br, with e.g. diethyl phosphite under reducing conditions, e.g. in the presence of NaH. The reaction may be performed in accordance with methods known in the art, e.g. as disclosed by G. Ösapay et al in supra.

In above reactions, the OH and amino protection may be performed simultaneously by reacting the free aminoalcohol or aminodiol of formula IIIa or IIIb in order to obtain a cyclic residue formed by the amino group and the alcohol group, e.g. oxazolidin-2-one, e.g. by reaction with Cbo-Cl, Boc-anhydride or phosgene under basic conditions.

Insofar as the production of the starting materials is not particularly described, the compounds are known or may be prepared analogously to methods known in the art or as disclosed in the Examples hereinafter. For example, compounds of formula IIIa or IIIb in protected or unprotected form, e.g. wherein $R_4$ has the significance of $R'_4$, may be prepared e.g. as disclosed in EP-A1-0 627 406, WO 96/06068 or EP-A1-1 002 792, the contents thereof being incorporated herein by reference.

Among the compounds of formula IIIa, the compounds of formula X

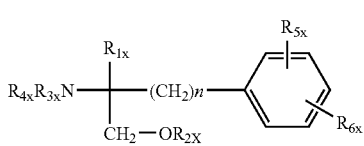

wherein n is 2, 3 or 4

$R_{1x}$ is H; $C_{1-6}$alkyl optionally substituted by OH, acyl, halogen, cycloalkyl, phenyl or hydroxy-phenylene; $C_{2-6}$alkenyl; $C_{2-6}$alkynyl; or phenyl optionally substituted by OH;

$R_{2x}$ is H, $C_{1-4}$alkyl or acyl each of $R_{3x}$ and $R_{4x}$, independently, is H, $C_{1-4}$alkyl optionally substituted by halogen or acyl, $R_{5x}$ is H, $C_{1-4}$alkyl or $C_{1-4}$alkoxy, and $R_{6x}$ is $C_{1-20}$alkanoyl substituted by cycloalkyl; cycloalkyl$C_{1-4}$alkoxy wherein the cycloalkyl ring is optionally substituted by halogen, $C_{1-4}$alkyl and/or $C_{1-4}$alkoxy; phenyl$C_{1-14}$alkoxy wherein the phenyl ring is optionally substituted by halogen, $C_{1-4}$alkyl and/or $C_{1-4}$alkoxy, $R_{6x}$ being also $C_{4-14}$alkoxy when $R_{1x}$ is $C_{3-4}$alkyl substituted by OH, or pentyloxy or hexyloxy when $R_{1x}$ is $C_{1-4}$alkyl, provided that $R_{6x}$ is other than phenyl-butylenoxy when either $R_{5x}$ is H or $R_{1x}$ is methyl, in free form or in salt form, are novel and form part of the invention.

$C_{4-14}$alkoxy as $R_{6x}$ is preferably $C_{5-10}$alkoxy.

Compounds of formula X may exist in free form or in salt form, e.g. addition salts with e.g. inorganic acids, such as hydrochloride, hydrobromide or sulfate, salts with organic acids, such as acetate, fumarate, maleate, benzoate, citrate, malate, methanesulfonate or benzenesulfonate salts. Compounds of formula X and their salts in hydrate or solvate forms form also part of the invention.

When the compounds of formula X have one or more asymmetric centers in the molecule, various optical isomers are obtained. The present invention also encompasses enantiomers, racemates, diastereoisomers and mixtures thereof. For example, the central carbon atom in formula X may have the R or S configuration. When the compounds of formula X include geometric isomers, the present invention embraces cis-compounds, trans-compounds and mixtures thereof. Similar considerations apply in relation to starting materials exhibiting asymmetric carbon atoms.

Compounds of formula X may be prepared in accordance with methods known in the art, e.g. as disclosed in EP-A1-0 778 263 or EP-A1-0 627 406, e.g by removing either a hydroxy-protecting group present in $R_1$, or in $R_2$, in a compound of formula X comprising a hydroxy-protecting group in $R_1x$ or in $R_2$ or an amino-protecting group present in $R_{4x}$ or $R_{3x}$ in a compound of formula X comprising an amino-protecting group in $R_{4x}$ or $R_{3x}$, e.g. as disclosed in Examples 17 to 27. If one of $R_{3x}$ or $R_{4x}$ is an amino-protecting group, then the other is preferably H. Compounds of formula X wherein each of $R_{1x}$ and $R_{2x}$ contain a terminal hydroxy, may also be prepared via an oxazolidin-2-one ring or a higher homolog intermediary step as disclosed in EP-A1-0 778,263. Where required, the compounds of formula X obtained in free form may be converted into the desired salt form, or vice versa. Compounds of formula X may be prepared e.g. according to following scheme:

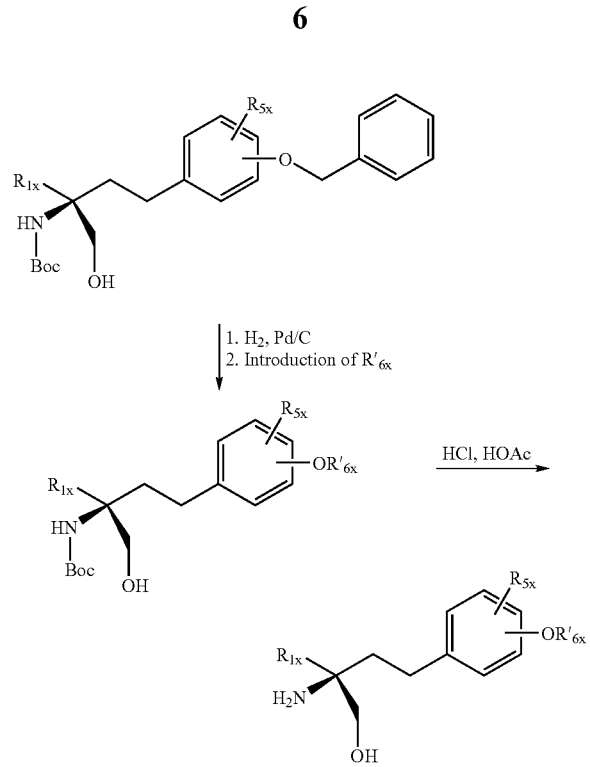

wherein $R'_{6x}$ is $C_{4-14}$alkyl, cycloalkyl$C_{1-14}$alkyl or phenyl$C_{1-14}$alkyl wherein the cycloalkyl or phenyl ring is optionally substituted as stated for $R_{6x}$. Compounds of formula X wherein $R_{6x}$ is $C_{1-20}$alkanoyl may be prepared starting with an aldehyde as disclosed in EP-A1-1 002 792 and followed by a Grignard reaction to introduce the desired $R_{6x}$ group.

Insofar as the production of the starting materials is not particularly described, the compounds are known or may be prepared analogously to methods known in the art or as disclosed in the Examples hereinafter, e.g. in example 6.

The following Examples are illustrative of the invention.

| | |
|---|---|
| RT = | room temperature |
| DMF = | Dimethylformamide |
| Fmoc = | 9-Fluorenyl methoxy carbonyl |
| Boc = | tert.-butoxy-carbonyl |
| Cbo = | Carboxybenzoxy |
| TEA = | Triethylamine |
| HOSu = | Hydroxysuccinimid |
| FTY720 = | 2-amino-2-[2-(4-octylphenyl) ethyl]propane-1,3-diol |

EXAMPLE 1

Phosphoric acid mono-{2-amino-2-hydroxymethyl-4-[4-(5-phenyl-pentanoyl)-phenyl]-butyl}ester

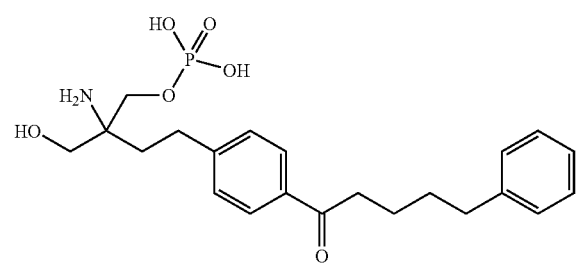

a) {1,1-Bis-hydroxymethyl-3-[4-(5-phenyl-pentanoyl)-phenyl]-propyl}-carbamic acid 9H-fluoren-9-ylmethyl ester 1-[4-(3-Amino-4-hydroxy-3-hydroxymethyl-butyl)-phenyl]-5-phenyl-pentan-1-one (1.07 g, 3 mmol) is dissolved in DMF/water (100 ml, 8/2). After addition of NaHCO$_3$ (1g) and FmocHOSu (1.21 g, 3.6 mmol) the reaction is kept at RT for 24 hours. The reaction is then poured in aqueous NaHCO$_3$ solution (6%, 500 ml) and the resulting precipitate is filtered off and dried. The resulting Fmoc protected compound is purified on silica gel using cyclohexane/ethyl acetate (1/1) as mobile phase.

[M+H]$^+$: 558 (ESI-MS).

b) {1-(Diphenoxy-phosphoryloxymethyl)-1-hydroxymethyl-3-[4-(5-phenyl-pentanoyl)-phenyl]-propyl}-carbamic acid 9H-fluoren-9-ylmethyl ester Compound of step a) (1.1 g, 2 mmol) is dissolved in dichloromethane (100 ml) and then treated with TEA (0.42 ml; 3 mmol) and diphenylphosporyl chloride (0.45 ml, 2.2 mmol). After 16 hours at RT the reaction medium is extracted with 0.5N HCl and the organic phase is separated, dried and concentrated. The crude compound is purified on silica gel using cyclohexane/ethyl acetate (3/1) as mobile phase.

[M+H]$^+$: 809 (ESI-MS).

c) Phosphoric acid mono-[2-amino-2-hydroxymethyl-4-(4-octyl-phenyl)-butyl]ester

Compound obtained in step b) (0.32 g, 0.4 mmol) is dissolved in ethanov/water (10 ml, 3/2) and, after addition of barium hydroxyde-octahydrate (0,56 mg, 1.8 mmol), is kept at 75° C. for 14 hours. After cooling to RT the slurry is neutralized with solid carbon dioxide and filtered. The residue is dissolved in acetic acid (95%; 5 ml) and then diluted with water to a volume of 50 ml. The resulting precipitate is filtered off and dried over P$_4$O$_{10}$.

NMR, CD$_3$OD+0.1N DCI, δ(ppm): 1.70 (m, 4H, ArCH$_2$CH$_2$CH$_2$CH$_2$), 2.02 (q, 2H, CH$_2$CH$_2$C), 2.65 (t, 2H, CH$_2$Ph), 2.78 (m, 2H, CH$_2$CO), 3.01 (t, 2H, COArCH$_2$), 3.73 (s, 2H, CH$_2$OH) 4.16 (2H, CH$_2$OP), 7.10-7.25 (m, 5H, arom. CH), 7.38 (d, 2H, arom. CH), 7.91 (d, 2H, arom. CH). MS: (ES−): 434.3 (M−H)$^-$

EXAMPLE 2

Phosphoric acid mono-{2-amino-4-[4-(5-cyclohexyl-pentanoyl)-phenyl]-2-hydroxymethyl-butyl}ester By following the procedure as disclosed in Example 1, but using the appropriate starting compounds, following compound is obtained:

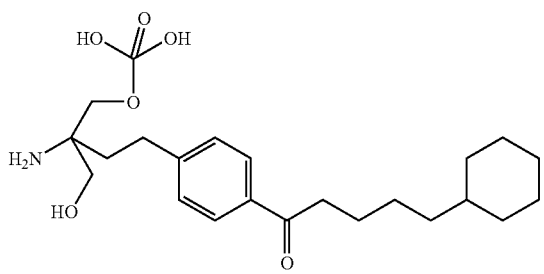

NMR, CD$_3$OD+0.1N DCI, δ(ppm): ). 85-1.80 (m, 15H, aliphatic H), 2.02 (m, 2H, CH$_2$CH$_2$C), 2.80 (m, 2H, CH$_2$Ph), 3.34 (t, 2H, CH$_2$CO), 3.74 (s, 2H, CH$_2$OH) 4.02 (t, 2H, CH$_2$OP), 7.43 (d, 2H, arom. CH), 7.95 (d, 2H, arom. CH), MS: (ES−): 440.3 (M−H)$^-$; MS: (ES+): 442.3 (MH$^+$)

EXAMPLE 3

Phosphoric acid mono-{2-amino-2-hydroxymethyl-4-[4-(1-hydroxy-5-phenyl-pentyl)-phenyl]-butyl}ester

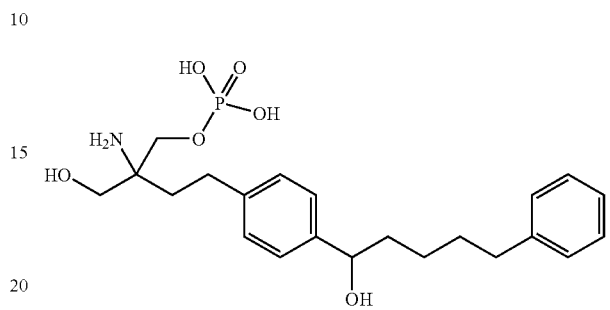

The compound is obtained by reducing the compound of Example 2 in protected form. MS (ES) 438.2 [M+H]$^+$

EXAMPLE 4

Phosphoric acid mono-{2-amino-2-hydroxymethyl-4-[4-(7-phenyl-heptanoyl)-phenyl]-butyl}ester By following the procedure as disclosed in Example 1, but using the appropriate starting compounds, following compound is obtained:

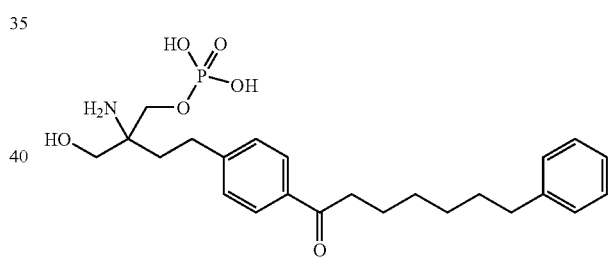

MS (ES) 463.2 [M+H]$^+$

EXAMPLE 5

Phosphoric acid mono-{2-amino-2-hydroxymethyl-4-[4-(7-phenyl-heptanoyl)-phenyl]-butyl}ester

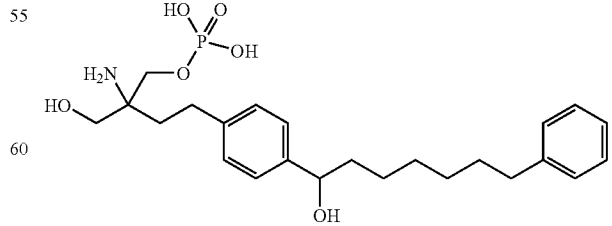

The compound is obtained by reducing the compound of Example 4 in protected form.
MS (ES) 464.2 [M+H]$^+$

EXAMPLE 6

Phosphoric acid mono{(R)-2-amino-4-[3-methoxy-4-(4-phenyl-butoxy)-phenyl]-2-methyl-butyl}ester

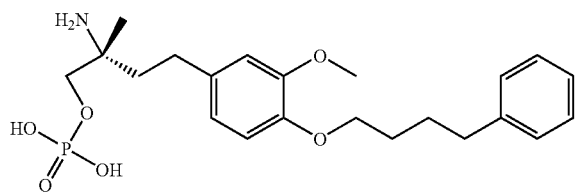

The endproduct of step i) (60 mg; 0.11 mmol) is treated with glacial acetic acid (1 ml) and concentrated HCl (0.1 ml) for 30 minutes at RT. After diluting with water (10 ml) the reaction mixture is freeze dried. Pure title compound is obtained without any further purification. MS (ES) 438.2 $[M+H]^+$.

a) 2-[3-Methoxy-4-(4-phenyl-butoxy)-phenyl]-ethanol

To a solution of homovanillyl alcohol (10 g, 59.3 mmol) in dry methanol (140 ml), there is added 12 ml of 1N $NaOCH_3$ in methanol. After addition of a solution of 1-bromo-4-phenylbutane (12.6 g, 59.3 mmol) in THF (10 ml) the reaction mixture is kept at reflux for 3 hours. After cooling the reaction is quenched with saturated aqueous $NaHCO_3$ and extracted with ethyl acetate (2 times, 500 ml each). The organic layer is dried over $MgSO_4$ and the solvent is removed by evaporation. The crude residue is then purified on silica gel using ethyl acetate/n-hexane (1/1) as mobile phase.

b) 4-(2-iodo-ethyl)-2-methoxy-1-(4-phenyl-butoxy)-benzene

Triethylamine (5.3 ml) is added to a solution of the endproduct of step a) (8.1 g; 27 mmol) in dry dichloromethane (150 ml). The reaction mixture is cooled to 0° C. and after addition of methanesulphonyl chloride (2.5 ml; 32.4 mmol) the reaction is kept at 0° C. for 30 minutes. After quenching with water the organic layer is dried over $MgSO_4$ and evaporated to yield a colourless oil. The residue is dissolved in dry acetone (200 ml) and NaI (5.3 g; 35.1 mmol) is added and the reaction mixture is kept at RT for 14 hours and then refluxed for 4 hours. After filtration and evaporation the residue is dissolved in ethyl acetate and extracted (2 times) with water. The organic phase is dried over $MgSO_4$ and the solvent is removed under reduced pressure. Recrystallisation from diethylether/hexane yields pure crystallized endproduct.

c) (2R,5S)-3,6-Diethoxy-2-isopropyl-5-{2-[3-methoxy-4-(4-phenyl-butoxy)-phenyl ]-ethyl}-2,5-dihydro-pyrazine

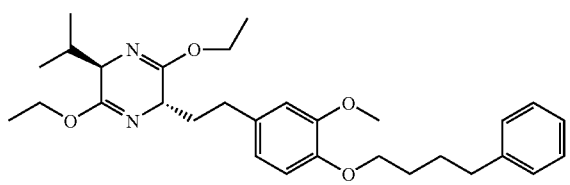

To a solution of (R)-3,6-diethoxy-2-isopropyl-2,5-dihydro-pyrazine (2.2 g; 10.4 mmol; Lohr, Birgit et al., Synlett, 1999, 7, 1139-1141) in dry THF (30 ml) at −78° C. there is added n-butyllithium (6.5 ml; 10.4 mmol; 1.6M in n-hexane). After 30 minutes at −78° C. the endproduct of step b) (4.3 g; 10.4 mmol) dissolved in dry THF (15 ml) is added tropwise over a period of 10 minutes. The reaction mixture is allowed to warm up to RT and it is kept at RT for 20 hours. After quenching with saturated aqueous ammonium chloride solution and extraction (2 times) with ethyl acetate the organic phase is dried over $MgSO_4$ and concentrated under reduced pressure. The crude is purified on silica gel using diethylether/n-hexane (1/9) as mobile phase.

d) (2R,5R)-3,6-Diethoxy-2-ethyl-5-isopropyl-2-{2-[3-methoxy-4-(4-phenyl-butoxy)-phenyl]-ethyl}-2,5-dihydro-pyrazine

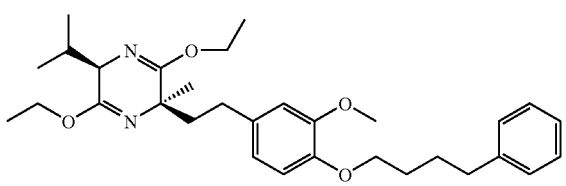

To a solution of the endproduct of step c) (2.5 g; 5.0 mmol) in dry THF (10 ml) at −78° C. there is added n-butyllithium (3.4 ml; 5.5 mmol; 1.6M in n-hexane). After 30 minutes at −78° C. methyliodide (0.37 ml; 6 mmol) dissolved In dry THF (15 ml) is added tropwise over a period of 10 minutes. The reaction mixture is allowed to warm up to RT and it is kept at RT for 3 hours. After quenching with saturated aqueous ammonium chloride solution and extraction (2 times) with ethyl acetate the organic phase is extracted with sodium thiosulphate solution, subsequently dried over $MgSO_4$ and concentrated under reduced pressure. The crude is purified on silica gel using diethylether/n-hexane (5/95) as mobile phase.

e) (R)-2-Amino-2-ethyl-4-[3-methoxy-4-(4-phenyl-butoxy)-phenyl]-butyric acid ethyl ester

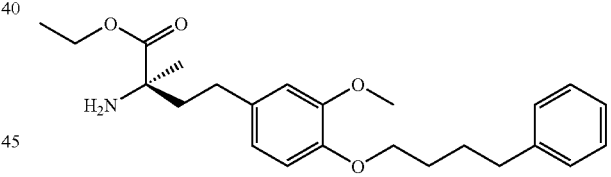

An aqueous solution of TFA (60 ml; 1M in water) is added to a solution of the endproduct of step d) (1.3 g; 3.0 mmol) in acetonitrile (90 ml). After 6 days at RT the clear solution is adjusted to pH 8 (saturated $NaHCO_3$ solution) and extracted with ethyl acetate (2 times). The organic layer is dried over $MgSO_4$, evaporated and the residue is purified on silica gel with pure ethyl acetate as mobile phase.

f) (R)-2-Amino-2-ethyl-4-[3-methoxy-4-(4-phenyl-butoxy)-phenyl]-butan-1-ol

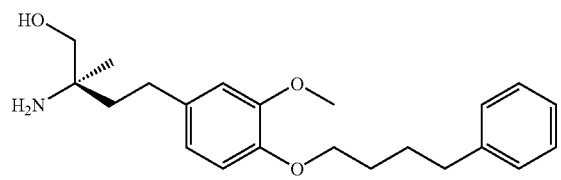

LiAlH₄ (1.13 ml; 1.13 mmol; 1M in THF) is added to a solution of the endproduct of step e) (0.31 g; 0.75 mmol) in dry THF (91 ml). After 30 minutes at reflux and cooling down to RT the reaction mixture is carefully quenched with 0.4 ml saturated aqueous Na₂SO₄ solution. After filtration the solution is evaporated under reduced pressure and the residue is purified on silica gel with ethyl acetate/methanol (9/1) as mobile phase. MS (ES+): 358.3 [MH⁺]

g) N-Boc-(R)-2-Amino-2-ethyl-4-[3-methoxy-4-(4-phenyl-butoxy)-phenyl]-butan-1-ol

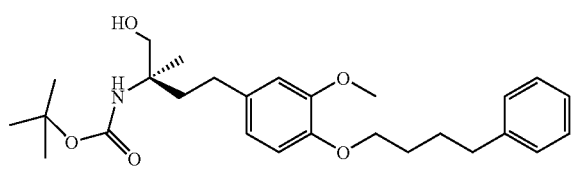

To a solution of (R)-2-Amino-2-ethyl-4-[3-methoxy-4-(4-phenyl-butoxy)-phenyl]-butan-1-ol (2.4 g; 6.5 mmol) in dichloromethane there is added triethylamine (1.08 ml; 7.8 mmol) and di-tert-butyl dicarbonate (1.56 g; 7.15 mmol). After further addition of dichloromethane (10 ml) and THF (5 ml) the reaction mixture is kept at RT for 14 hours. The solvents are evaporated under reduced pressure and pure title compound is obtained by recrystallisafion from ethyl acetate/n-hexane. MS (ES) 458.3 [M+H]⁺ h) [(R)-3-[3-Methoxy-4-(4-phenyl-butoxy)-phenyl]-1-methyl-1-(3-oxo-1,5-dihydro-3λ*5*-benzo[e][1,3,2]dioxaphosphepin-3-yloxymethyl)-propyl]-carbamic acid tert-butyl ester

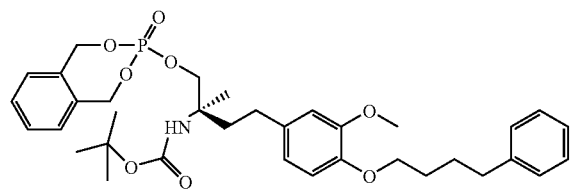

To a solution of N-Boc-(R)-2-Amino-2-ethyl-4-[3-methoxy-4-(4-phenyl-butoxy)-phenyl]-butan-1-ol (0.23 g; 0.5 mmol) in THF (5 ml) is added N,N-diethyl-1,5-dihydro-2,4,3-benzodioxaphosphepin-3-amine (0.24 g; 1 mmol) and tetrazole (0.11 g; 1.5 mmol). After 2 hours at RT H₂O₂ (30% in water; 0.58 ml) is added and the mixture is kept at RT for further two hours. The reaction mixture is quenched with Na₂S₂O₃ and extracted with ethyl acetate and then washed with aqueous citric acid and aqueous saturated NaHCO₃ solution. The organic layer is dried and concentrated and then purified on a silica gel using dichloromethane/ethanol (95/5) as mobile phase.

i) {(R)-3-[3-Methoxy-4-(4-phenyl-butoxy)-phenyl]-1-methyl-1-phosphonooxymethyl-propyl}-carbamic acid tert-butyl ester

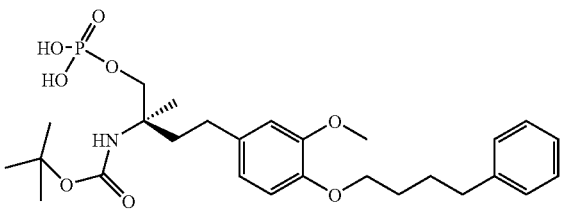

The endproduct of step h) (82 mg; 0.13 mmol) is dissolved in ethanovethyl acetate (30 ml 2/1) and hydrogenated with Pd/C₁₀% as catalyst under normal pressure for two hours. After filtering and evaporation the title compound is isolated as a colorless oil.

MS (ES) 538,3 [M+H]⁺.

EXAMPLE 7

Phosphoric acid mono-{(R)-2-amino-2-ethyl-4-[3-methoxy-4-(phenyl-butoxy)-phenyl]-butyl}ester

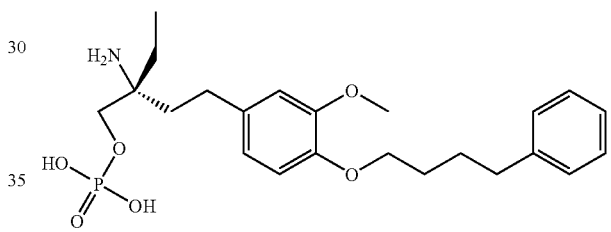

Ethyl iodide is used instead of methyl iodide in step d) of example 6. MS (ES) 452.2 [M+H]⁺

EXAMPLE 8

Phosphoric acid mono-{(R)-2-amino-2-methyl-4-[4-(3-phenyl-propoxy)-phenyl]-butyl}ester

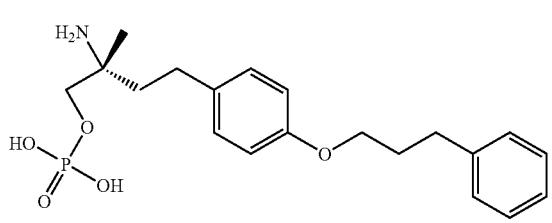

The endproduct of step f) below is treated with glacial acetic acid (1 ml) and concentrated HCl (0.1 ml) for 30 minutes at RT. After diluting with water (10 ml) the reaction mixture is freeze dried. Pure title compound is obtained without any further purification.

NMR, DMSO, δ(ppm): 1.29 (s, 3H, CCH₃), 1.82 (m, 2H, CCH₂), 2.02 (pent, 2H, CH₂CH₂CH₂), 2.58 (m, 2H, CH₂PhO), 2.77 (t, 2H, PhCH₂), 3.80-3.98 (4H, CH₂O), 6.88 (d, 2H, arom. CH), 7.12 (d, 2H, arom. CH), 7.18-7.35 (m, 5H, arom. CH). MS (ES−): 785.3 (2M−H), 392.3 (M−H).

a) (R)-2-Amino-4-(4-benzyloxy-phenyl)-2-methyl-butan-1-ol

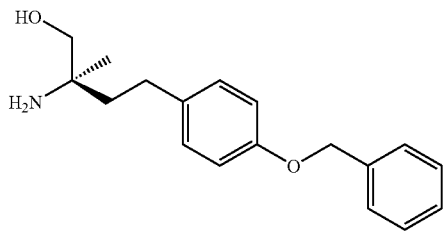

2-[4-(benzyloxy)phenyl]ethyl bromide is used instead of 4-(2-iodo-ethyl)-2-methoxy-1-(4-phenyl-butoxy)-benzene in step c) of example 6). MS (ES) 286.2 [M+H]+.

b) N-Boc-(R)-2-amino-4-(4-benzyloxy-phenyl)-2-methyl-butan-1-ol

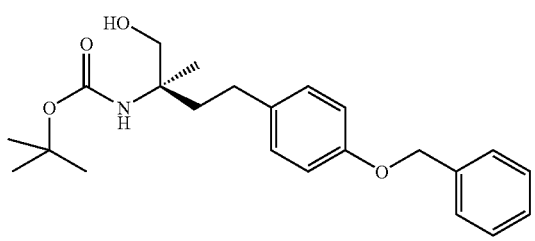

To a solution of (R)-2-amino-4-(4-benzyloxy-phenyl)-2-methyl-butan-1-ol (1.85 g; 6.5 mmol) in dichloromethane is added triethylamine (1.08 ml; 7.8 mmol) and di-tert-butyl dicarbonate (1.56 g; 7.15 mmol). After further addition of dichloromethane (10 ml) and THF (5 ml) the reaction mixture is kept at RT for 14 hours. The solvents are evaporated under reduced pressure and pure title compound is obtained by recrystallisation from ethyl acetate/n-hexane. MS (ES) 386.2 [M+H]+ c) N-Boc-(R)-2-Amino-4-(4-hydroxy-phenyl)-2-methyl-butan-1-ol

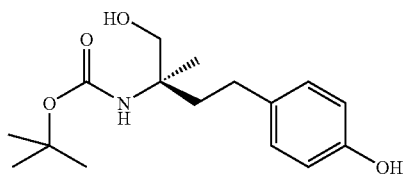

A solution of the endproduct of step i) (2.4 g; 6.2 mmol) in ethanol (240 ml) is hydrogenated over Pd/C$_{10\%}$ (300 mg) at normal pressure. After three hours the catalyst is filtered off and the filtrate is concentrated under reduced pressure. Purification is achieved by recrystallisation from ethano/diethylether/n-hexane. MS (ES) 296.2 [M+H]+.

d) N-Boc-(R)-2-Amino-2-methyl-4-[4-(3-phenyl-propoxy)-phenyl]-butan-1-ol

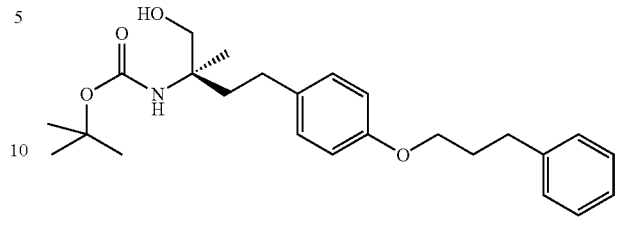

K$_2$CO$_3$ (233 mg; 1.7 mmol) and (3-bromo-propyl)-benzene (0.16 g; 0.82 mmol) are added to a solution of the endproduct of step b) (200 mg; 0.68 mmol) in ethanol (4 ml). After 6 hours at 50° C. additional (3-bromo-propyl)-benzene (0.1 g; 0.82 mmol) is added and the reaction mixture is kept at 50° C. for further 14 hours. After cooling the reaction is diluted with ethyl acetate and extracted with water (2 times). The organic phase is dried over MgSO$_4$, concentrated and the crude is purified on silica gel using diethylether/n-hexane as mobile phase. MS (ES) 413.3 [M+H]+ e) & f) {(R)-1-Methyl-3-[4-(3-phenyl-propoxy)-phenyl]-1-phosphonooxymethyl-propyl}-carbamic acid tert-butyl ester

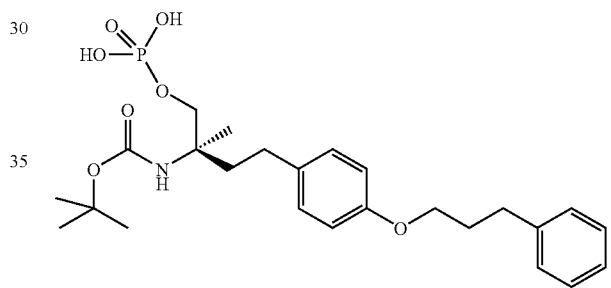

The synthesis is performed according to step h) & i) described in example 6.
MS (ES) 494.2 [M+H]+.

EXAMPLE 9

Phosphoric Acid Mono{(R)-2-amino-4-[4-(4-ethyl-benzyloxy)-phenyl]-2-methyl-butyl}ester

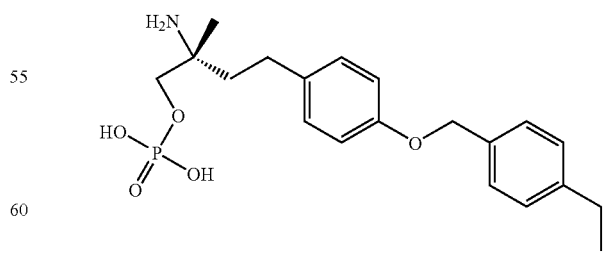

The synthesis is performed according to the procedure of example 8 using the mesylate of (4-ethyl-phenyl)-methanol instead of (3-bromo-propyl)-benzene in step d)
MS (ES) 394.2 [M+H]+.

EXAMPLE 10

Phosphoric acid mono-((R)-2-amino-{4-[3-(4-methoxy-phenyl)-propoxy]-phenyl}-2-methyl-butyl)ester

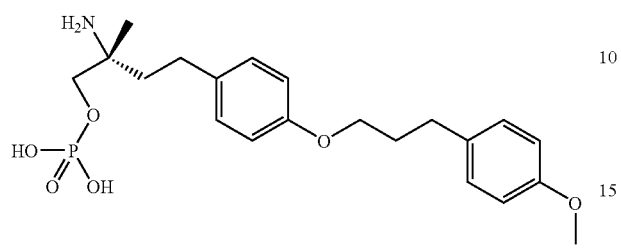

The synthesis is performed according to the procedure of example 8 using the mesylate of 3-(4-methoxy-phenyl)-propan-1-ol instead of (3-bromo-propyl)-benzene in step d). MS (ES) 324.2 [M+H]+.

EXAMPLE 11

Phosphoric acid mono-{(R)-2-amino-4-[4-(3-cyclohexyl-propoxy)-phenyl]-2-methyl-butyl}ester

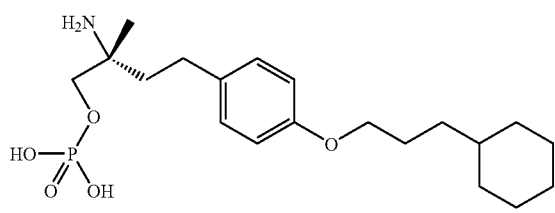

The synthesis is performed according to the procedure of example 8 using the mesylate of 3-cyclohexyl-propan-1ol instead of (3-bromo-propyl)-benzene in step d).
MS (ES) 400.2 [M+H]+.

EXAMPLE 12

Phosphoric acid mono-{(R)-2-amino-2-methyl-4-[4-(5-phenyl-pentyloxy)-phenyl]-butyl}ester

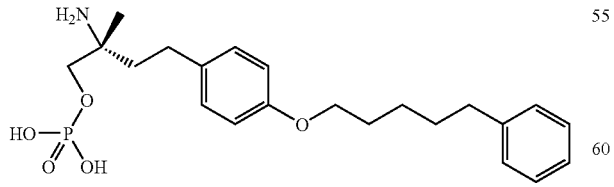

The synthesis is performed according to the procedure of example 8 using 1-bromo-5-phenylpentane instead of (3-bromo-propyl)-benzene in step d). MS (ES) 422.2 [M+H]+.

EXAMPLE 13

Phosphoric acid mono-{(R)-2-amino-2-methyl-4-[4-(4-phenyl-butoxy)-phenyl]-butyl}ester

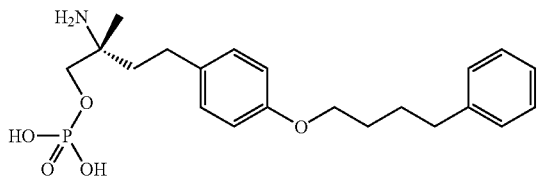

The synthesis is performed according to the procedure of example 8 using 1-bromo-4-phenylbutane instead of (3-bromo-propyl)-benzene in step d). MS (ES) 408.2 [M+H]+.

EXAMPLE 14

Phosphoric acid mono-{(S)-2-amino-2-[2-(4-heptyloxy-phenyl)-ethyl]-pent-4-ynyl}ester

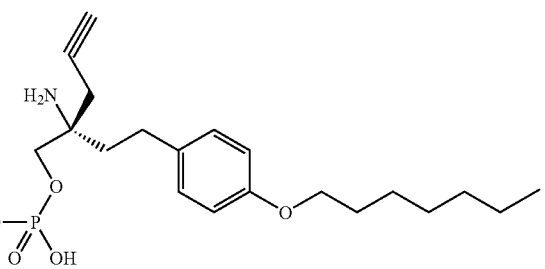

The synthesis is performed according to the procedure of example 6 using 1-heptyloxy-4-(2-iodo-ethyl)-benzene instead of 4-(2-iodo-ethyl)-2-methoxy-1-(4-phenyl-butoxy)-benzene in step c) and using 3-bromo-1-propyne instead of methyliodide in step d). NMR, DMSO, δ(ppm): 0.90 (t, 3H, CH$_2$CH$_3$), 1.22-1.45 (br, 8H, (CH$_2$)$_4$), 1.70 (pent, 2H, CH$_2$CH$_2$O), 1.90 (m, 2H, CCH$_2$), 2.59 (m, 2H, CH$_2$Ph), 2.67 (d, 2H, HCCCH$_2$), 3.18 (CCH), 3.93 (m, 4H, CH$_2$O), 6.87 (d, 2H, arom. CH), 7.12 (d, 2H, arom. CH). MS (ES−): 793.3 (2M−H), 396 (M−H); MS (ES+): 795.3 (2M+H), 398.3 (MH).

EXAMPLE 15

Phosphoric acid mono-[(R)-2-amino-2-methyl-4-(4-pentyloxy-phenyl)-butyl]ester)

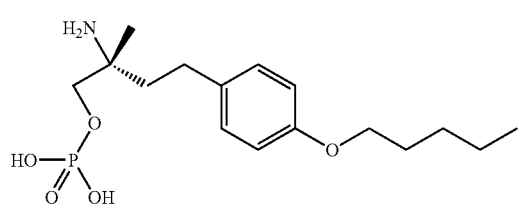

NMR, DMSO, δ(ppm): 0.92 (t, 3H, CH$_2$CH$_3$), 1.29 (s, 3H, CCH$_3$), 1.30-1.50 and 1.65-1.95 (br, 8H, CH$_2$CH$_2$CH$_2$, CCH₂), 2.55 (m, 2H, CH₂Ph), 3.80-3.98 (4H, CH₂O), 6.87 (d, 2H, arom. CH), 7.12 (d, 2H, arom. CH). MS (ES-): 689.3 (2M-H), 380 (M+Cl), 344 (M-H).

EXAMPLE 16a

Phosphoric acid mono[(R)-2-amino-4-(4-hexyloxy-phenyl)-2-methyl-butyl]ester

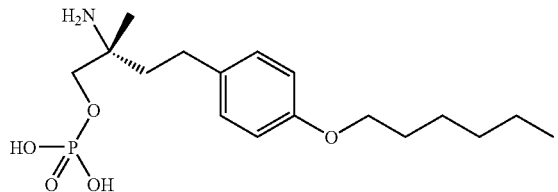

MS (ES) 360.4 [M+H]⁺.

EXAMPLE 16b

Phosphoric acid mono-[(R)-2-amino-2-ethyl-4-(4-heptyloxy-phenyl)-butyl]ester

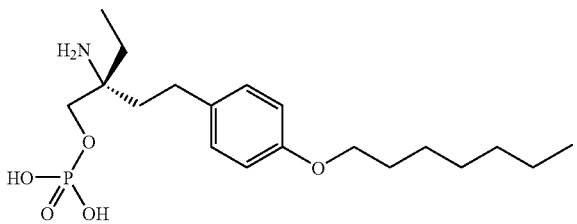

NMR, DMSO, δ(ppm): 0.91 (2x t, 6H, CCH₃, CH₂CH₃), 1.23-1.48 and 1.64-1.83 (br, 14H, CH₂CH₃, CCH₂, (CH₂)₅), 2.55 (m, 2H, CH₂Ph), 3.93 (m, 4H, CH₂O), 6.87 (d, 2H, arom. CH), 7.12 (d, 2H, arom. CH). MS (ES-): 773.4 (2M-H), 386.3 (M-H).

EXAMPLE 17

(R)-2-Amino-2-ethyl-4-[3-methoxy-(4-phenyl-butoxy)-phenyl]-butan-1-ol

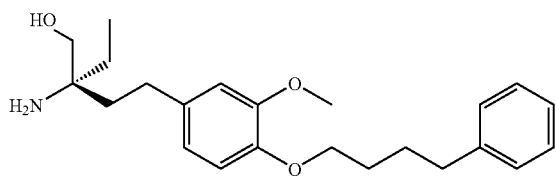

The title compound is prepared by following the procedure of Example 6, steps a) to f), except that ethyl iodide (0.48ml; 6 mmol) is used instead of methyl iodide in step d).

MS (ES+): 372.3 [MH⁺]

EXAMPLE 18

(R)-2-Ethyl-4-(4-heptyloxy-phenyl)-2-methylamino-butan-1-ol

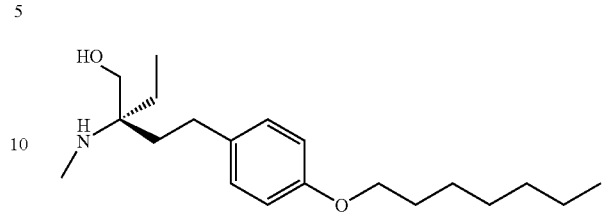

Using 1-heptyloxy-4-(2-iodo-ethyl)-benzene (as disclosed in WO 9408943 A1) instead of 4-(2-iodo-ethyl)-2-methoxy-1-(4-phenyl-butoxy)-benzene in step c) of example 6.

MS (ES+): 322.3 [MH⁺].

N-methylation of (R)-2-amino-2-ethyl-4-(4-heptyloxy-phenyl)-butyric acid ethyl ester is performed as follows:

(R)-2-amino-2-ethyl-4-(4-heptyloxy-phenyl)-butyric acid ethyl ester (175 mg; 0.5 mmol) is dissolved in dichloromethane (2) and formic acid (100 μl), p-formaldehyde (100 μl; 30% in water) and NaBH₃CN are added. After 1 hour at RT the reaction mixture is extracted with saturated aqueous NaHCO₃ solution and the organic layer is dried over MgSO₄ and purified on silica gel using n-hexanetethyl acetate (1/1→1/9) as mobile phase.

EXAMPLE 19

(S)-2-Amino-2-(2-benzyloxy-ethyl)4-heptyloxy-phenyl)-butan-1-ol

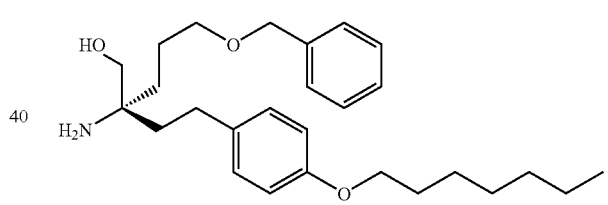

Using 1-heptyloxy-4-(2-iodo-ethyl)-benzene instead of 4-(2-iodo-ethyl)-2-methoxy-1-(4-phenyl-butoxy)-benzene in step c) and benzyl (3-bromo-propoxymethyl)-benzene instead of ethyliodide in step d) of example 6).

MS (ES+): 428.3 [MH⁺].

EXAMPLE 20

(S)-2-Amino-2-[2-(4-heptyloxy-phenyl)-ethyl]-butane-1,4-diol

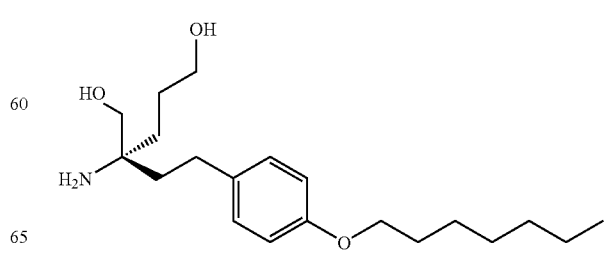

A solution of the endproduct of example 19 (43 mg; 0.1 mmol) in ethanol (2.5 ml) is hydrogenated over Pd(OH)$_2$ (120 mg added in 3 portions) at normal pressure. After three days the catalyst is filtered off and the solution is concentrated under reduced pressure. Purification of the crude on silica gel with tert.-butylmethylether/methanol/NH$_4$OH$_{25\%}$ (90/10/1→75/25/1) yields pure endproduct. MS (ES+): 338.3 [MH$^+$].

EXAMPLE 21

(R)-2-Amino-2-methyl-4-(4-pentyloxy-phenyl)-butan-1-ol

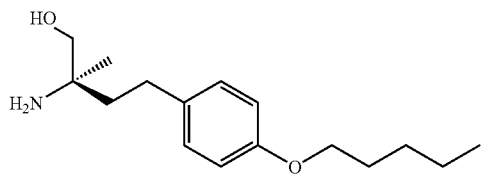

The endproduct of step iii) (50 mg; 0.14 mmol) is treated with glacial acetic acid (0.5 ml) and concentrated HCl (0.05 ml) at RT for 20 minutes. The reaction mixture is diluted with ethyl acetate (2 ml) and then treated with diethylether (20 ml) to afford a white precipitate. The precipitate is filtered off and washed 2 times with diethylether and dried. MS (ES+): 266.2 [MH$^+$].

i) N-Boc-(R)-2-Amino-4-(4-benzyloxy-phenyl)-2-methyl-butan-1-ol prepared as disclosed in example 8b)
ii) N-Boc-(R)-2-Amino-4-(4-hydroxy-phenyl)-2-methyl-butan-1-ol prepared as disclosed in example 8c)
iii) N-Boc-(R)-2-Amino-4-(4-pentyloxy-phenyl)-2-methyl-butan-1-ol To a solution of the endproduct of step ii) (200 mg; 0.68 mmol) in ethanol (4 ml) are added K$_2$CO$_3$ (233 mg; 1.7 mmol) and 1-iodopentane (0.11 ml; 0.82 mmol). After 6 hours at 50° C. additional 1-iodopentane (0.11 ml; 0.82 mmol) is added and the reaction mixture is kept at 50° C. for further 14 hours. After cooling the reaction is diluted with ethyl acetate and extracted with water (2 times). The organic phase is dried over MgSO$_4$, concentrated and the crude is purified on silica gel using diethylether/n-hexane as mobile phase.

EXAMPLE 22

(R)-2-Amino-2-methyl-4-[4-(5-phenyl-pentyloxy)-phenyl]-butan-1-ol

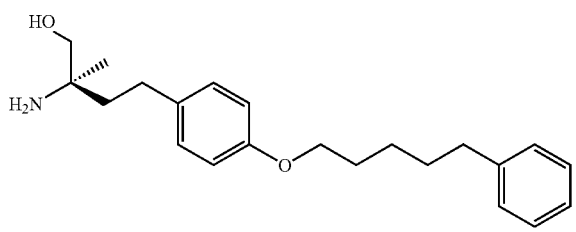

Using 1-bromo-5-phenyl-n-pentane instead of 1-iodopentane in step iii) of example 21).
MS (ES+): 342.3 [MH$^+$].

EXAMPLE 23

(R)-2-Amino-2-methyl-4-[4-(3-phenyl-propoxy)-phenyl]-butan-1-ol

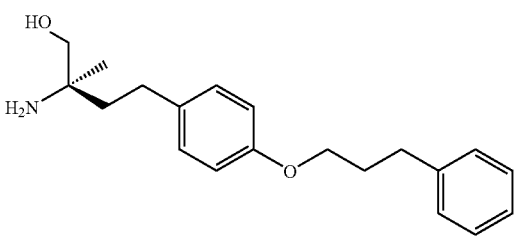

Using 1-bromo-3-phenyl-propane instead of 1-iodopentane in step iii) of example 21).
MS (ES+): 314.2 [MH$^+$].

EXAMPLE 24

(R)-2-Amino-4-[4-(4-ethyl-benzyloxy)-phenyl]-2-methyl-butan-1-ol

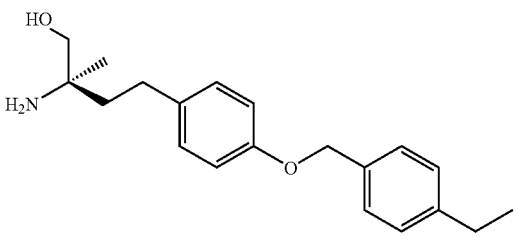

Using the mesylate of (4-ethyl-phenyl)-methanol [synthesized according to example 6)—step b)] instead of 1-iodopentane in step iii) of example 21).
MS (ES+): 314.2 [MH$^+$].

EXAMPLE 25

(R)-2-Amino-4-[4-(4-ethyl-benzyloxy)-phenyl]-2-methyl-butan-1-ol

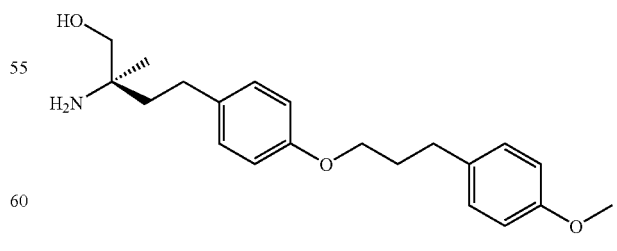

Using the mesylate of 3-(4-methoxy-phenyl)-propan-1-ol [synthesized according to example 6)—step b)] instead of 1-iodopentane in step iii) of example 21).
MS(ES+): 344.2 [MH$^+$].

EXAMPLE 26

(R)-2-Amino-4-[4-(3-cyclohexyl-propoxy)-phenyl]-2-methyl-butan-1-ol

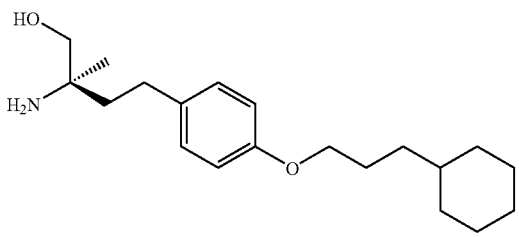

Using the mesylate of 3-cyclohexyl-propan-1-ol [synthesized according to example 6)—step b)] instead of 1-iodopentane in step iii) of example 21). MS(ES+): 320.3 [NH+].

EXAMPLE 27

1-[4-(3-Amino-4-hydroxy-3-hydroxymethyl-butyl)-phenyl]-5-cyclohexyl-pentan-1-one

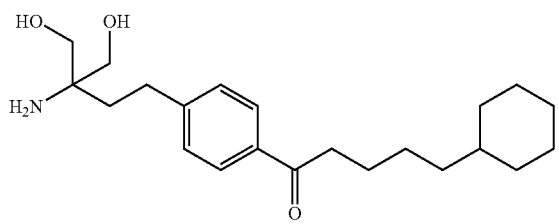

The compound is synthesized according to U.S. Pat. No. 6,214,873 B1 (col. 20) using (4-bromo-butyl)-cyclohexane instead of (4-bromo-butyl)-benzene for the Grignard reaction.

MS(ES+): 362.3 [NH+].

The compounds of formula I and the compounds of formula X, in free form or in pharmaceutically acceptable salt form, (hereinafter collectively "compounds of the invention") exhibit valuable pharmacological properties, e.g. lymphocyte recirculation modulating properties, e.g. as indicated in in vitro and in vivo tests and are therefore indicated for therapy.

A. In vitro

The compounds of the invention have binding affinity to individual human S1P receptors as determined in following assays:

Transient Transfection of Human S1P Receptors into HEK293 Cells

EDG receptors and $G_i$ proteins are cloned, and equal amounts of 4 cDNAs for the EDG receptor, $G_i$-α, $G_i$-β and $G_i$-γ are mixed and used to transfect monolayers of HEK293 cells using the calcium phosphate precipitate method (M. Wigler et al., Cell. 1977,;11;223 and DS. Im et al., Mol. Pharmacol. 2000;57;753). Briefly, a DNA mixture containing 25 μg of DNA and 0.25 M CaCl is added to HEPES-buffered 2 mM $Na_2HPO_4$. Subconfluent monolayers of HEK293 cells are poisoned with 25 mM chloroquine, and the DNA precipitate is then applied to the cells. After 4 h, the monolayers are washed with phosphate-buffered saline and refed media (90% 1:1 Dulbecco's modified essential media (DMEM):F-12+10% fetal bovine serum). The cells are harvested 48-72 h after addition of the DNA by scraping in HME buffer (in mM: 20 HEPES, 5 $MgCl_2$, 1 EDTA, pH 7.4) containing 10% sucrose on ice, and disrupted using a Dounce homogenizer. After centrifugation at 800×g, the supernatant is diluted with HME without sucrose and centrifuged at 100,000×g for 1 h. The resulting pellet is rehomogenized and centrifuged a second hour at 100,000×g. This crude membrane pellet is xresuspended in HME with sucrose, aliquoted, and snap-frozen by immersion in liquid nitrogen. The membranes are stored at 70° C. Protein concentration is determined spectroscopically by Bradford protein assay.

GTPγS Binding Assay Using S1P Receptor/HEK293 Membrane Preparations

GTPγS binding experiments are performed as described by DS. Im et al., Mol. Pharmacol. 2000; 57:753. Ugand-mediated GTPγS binding to G-proteins is measured in GTP binding buffer (in mM: 50 HEPES, 100 NaCl, 10 $MgCl_2$, pH 7.5) using 25 μg of a membrane preparation from transiently transfected HEK293 cells. Ligand is added to membranes in the presence of 10 μM GDP and 0.1 nM [$^{35}$S]GTPγS (1200 Ci/mmol) and incubated at 30° C. for 30 min. Bound GTPγS is separated from unbound using the Brandel harvester (Gaithersburg, Md.) and counted with a liquid scintillation counter.

In these assays, the compounds of the invention have binding affinities to S1P receptors in the sub-microM range.

B. In vivo: Blood Lymphocyte Depletion

A compound of the invention or the vehicle is administered orally by gavage to rats. Tail blood for hematological monitoring is obtained on day—1 to give the baseline individual values, and at 2, 6, 24, 48 and 72 hours after drug application. In this assay, the compounds of the invention deplete peripheral blood lymphocytes when administered at a dose of 0.03 to 3 mg/kg. For example, Compound of Examples 1, 2, 6f, 20, 22, 23, 26 depletes peripheral blood lymphocytes by more than 50% 24 hours after administration of a dose of 0.4; 0.6; 0.5; 0.1; 0.05; 0.2; and 0.3 mg/kg, respectively.

The compounds of the invention are, therefore, useful in the treatment and/or prevention of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, others, cancer, e.g. T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus. Compounds of the invention do not show the negative chronotropic effects as does sphingosine-1 phosphate.

For the above uses the required dosage will of course vary depending on the mode of administration, the particular condition to be treated and the effect desired. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 1 to 50 mg active ingredient.

The compounds of the invention may be administered by any conventional route, in particular enterally, e.g. orally, e.g. in the form of tablets or capsules, or parenterally, e.g. in the form of Injectable solutions or suspensions, topically, e.g. in the form of lotions, gels, ointments or creams, or in a nasal or a suppository form. Pharmaceutical compositions comprising a compound of the invention in free form or in pharmaceutically acceptable salt form in association with at least one pharmaceutical acceptable carrier or diluent may be manufactured in conventional manner by mixing with a pharmaceutically acceptable carrier or diluent.

The compounds of the invention may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by lymphocytes, e.g. such as indicated above, in a subject in need of such treatment, which method comprises administering to said subject an effective amount of a compound of the invention or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of the invention or a pharmaceutically acceptable salt thereof;

2. A compound of the invention, in free form or in a pharmaceutically acceptable salt form for use as a pharmaceutical, e.g. in any of the methods as indicated under 1.1 or 1.2 above.

3. A pharmaceutical composition, e.g. for use in any of the methods as in 1.1 or 1.2 above comprising a compound of the invention in free form or pharmaceutically acceptable salt form in association with a pharmaceutically acceptable diluent or carrier therefor.

4. A compound of the invention or a pharmaceutically acceptable salt thereof for use in the preparation of a pharmaceutical composition for use in any of the method as in 1.1 or 1.2 above.

The compounds of the invention may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell antiproliferative agent. For example, the compounds of the invention may be used in combination with a calcineurin inhibitor, e.g. cyclosporin A or FK 506; a mTOR inhibitor, e.g. rapamycin, 40-O-(2-hydroxyethyl)-rapamycin, CCI779 or ABT578; an ascomycin having immunosuppressive properties, e.g. ABT-281, ASM981, etc.; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40, CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil.

Where the compounds of the invention are administered in conjunction with other immunosuppressive/immunomodulatory, anti-inflammatory or chemotherapeutic therapy, dosages of the co-administered immunosuppressant, immunomodulatory, anti-inflammatory or chemotherapeutic compound will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a compound of the invention and at least a second drug substance, e.g. an immunosuppressant, immunomodulatory, anti-inflammatory or chemotherapeutic drug, e.g. as indicated above.

6. A pharmaceutical combination, e.g. a kit, comprising a) a first agent which is a compound of the invention as disclosed herein, in free form or in pharmaceutically acceptable salt form, and b) at least one co-agent, e.g. an immunosuppressant, immunomodulatory, anti-inflammatory or chemotherapeutic drug. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the invention and a co-agent, are both administered to a patient simultaneously in the form of a single entity or dosage. The term "non-fixed combination" means that the active ingredients, e.g. a compound of the invention and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

A preferred compound of the invention is the compound of Example 1.

The invention claimed is:

1. A compound of formula I

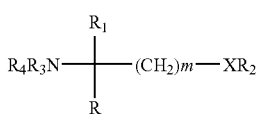

I wherein m is 1, 2 or 3;

X is O $R_1$ is H; $C_{1-6}$ alkyl optionally substituted by OH, acyl, halogen, cycloalkyl, phenyl or hydroxy-phenylene; $C_{2-6}$alkenyl; $C_{2-6}$alkynyl; or phenyl optionally substituted by OH;

$R_2$ is

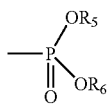

wherein $R_5$ is H or $C_{1-4}$alkyl optionally substituted by 1, 2 or 3 halogen atoms, and $R_6$ is H or $C_{1-4}$alkyl optionally substituted by halogen;

each of $R_3$ and $R_4$, independently, is H, $C_{1-4}$alkyl optionally substituted by halogen, or acyl, and R is a residue of formula (a)

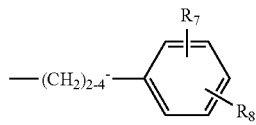

(a)

wherein $R_7$ is H, $C_{1-4}$alkyl or $C_{1-4}$alkoxy, and $R_8$ is (a) $C_{1-20}$alkanoyl, or $C_{1-14}$alkoxy substituted with cycloalkyl or phenyl wherein the cycloalkyl or phenyl ring is optionally substituted by halogen, $C_{1-4}$alkyl and/or $C_{1-4}$alkoxy, (b) phenyl$C_{1-14}$alkyl wherein the $C_{1-14}$alkyl is optionally substituted by halogen or OH, (c) cycloalkyl$C_{1-14}$alkoxy or phenyl$C_{1-14}$alkoxy wherein the cycloalkyl or phenyl ring is optionally substituted by halogen, $C_{1-4}$alkyl and/or $C_{1-4}$alkoxy, or (d) phenyl$C_{1-4}$alkoxy$C_{1-4}$alkyl, phenoxy$C_{1-14}$alkoxy or phenoxy$C_{1-4}$alkyl, in free form or in salt form.

2. A compound according to claim 1 which is selected from phosphoric acid mono-{2-amino-2-hydroxymethyl-4-[4-(5-phenyl-pentanoyl)-phenyl]-butyl}ester, phosphoric acid mono-{2-amino-4-[4-(5-cyclohexyl-pentanoyl)-phenyl]-2-hydroxymethyl-butyl}ester, phosphoric acid mono-{2-amino-2-hydroxymethyl-4-[4-(7-phenyl-heptanoyl)-phenyl]-butyl}ester, phosphoric acid mono-{(R)-2-amino-4-[3-methoxy-4-(4-phenyl-butoxy)-phenyl]-2-methyl-butyl}ester, phosphoric acid mono-{(R)-2-amino-2-methyl-4-[4-(5-phenyl-pentyloxy)-phenyl]-butyl}ester and phosphoric acid mono-[(R)-2-amino-4-(4-hexyloxy-phenyl)-2-methyl-butyl]ester, or a salt thereof.

3. A compound according to claim 1, in free form or in a pharmaceutically acceptable salt form for use as a pharmaceutical.

4. A pharmaceutical composition comprising a compound according to claim 1 in free form or pharmaceutically acceptable salt form in association with a pharmaceutically acceptable diluent or carrier therefor.

* * * * *